(12) United States Patent
Conlan et al.

(10) Patent No.: US 11,002,040 B2
(45) Date of Patent: May 11, 2021

(54) SANITIZER APPARATUS

(71) Applicant: Kenneth Conlan, Ratoath (IE)

(72) Inventors: Kenneth Conlan, Ratoath (IE); Joseph Clifford, Enfield (IE)

(73) Assignee: Kenneth Conlan, Ratoath (IE)

( * ) Notice: Subject to any disclaimer, the term of this patent is extended or adjusted under 35 U.S.C. 154(b) by 483 days.

(21) Appl. No.: 15/571,888

(22) PCT Filed: May 9, 2016

(86) PCT No.: PCT/EP2016/060355
§ 371 (c)(1),
(2) Date: Nov. 6, 2017

(87) PCT Pub. No.: WO2016/177912
PCT Pub. Date: Nov. 10, 2016

(65) Prior Publication Data
US 2018/0135332 A1 May 17, 2018

(30) Foreign Application Priority Data
May 7, 2015 (IE) .................................. S2015/0141

(51) Int. Cl.
*E05B 1/00* (2006.01)
*A61L 2/26* (2006.01)
(52) U.S. Cl.
CPC .............. *E05B 1/0069* (2013.01); *A61L 2/26* (2013.01)
(58) Field of Classification Search
CPC .................................. E05B 1/0069; A61L 2/26
See application file for complete search history.

(56) References Cited

U.S. PATENT DOCUMENTS

| 5,154,264 A | * | 10/1992 | Poertzgen | ................. A47C 3/30 188/285 |
| 6,874,697 B2 | * | 4/2005 | Callueng | ................... A61L 2/22 222/52 |
| 7,338,646 B2 | * | 3/2008 | Gilbert | ...................... A61L 2/18 16/412 |
| 7,989,779 B1 | | 8/2011 | Ray et al. | |

(Continued)

FOREIGN PATENT DOCUMENTS

| CN | 2110676 U | 7/1992 |
| DE | 202004006845 U1 | 9/2004 |
| DE | 202010009480 U1 | 9/2010 |

(Continued)

OTHER PUBLICATIONS

Search Report for Application No. CN201680026403 by the National Intellectual Property Administration, PRC.

(Continued)

*Primary Examiner* — Regina M Yoo
(74) *Attorney, Agent, or Firm* — Michael Crilly, Esquire

(57) ABSTRACT

A sanitizer apparatus for a handle on a door has a sanitary fluid reservoir and associated atomizing pump which discharges to one or more spray heads. A pump actuating means is operatively connected to the door handle so operation of the door handle operates the pump to spray disinfectant at the handle. The pump actuating means includes a time delay mechanism so that a person opening the door will have removed their hand from the handle before spraying commences.

18 Claims, 13 Drawing Sheets

(56) References Cited

U.S. PATENT DOCUMENTS 8,408,423 B1    4/2013  McKnight et al.
9,271,611 B2 *  3/2016  Stratmann ................ A47K 5/12

FOREIGN PATENT DOCUMENTS

| DE | 202012002226 U1 | 5/2012 |
| GB | 1450427 A | 9/1976 |
| WO | 03/012228 A1 | 2/2003 |
| WO | 2006074454 A2 | 7/2006 |
| WO | 2007070512 A3 | 12/2007 |
| WO | 2013/153168 A1 | 10/2013 |
| WO | 2014035610 A1 | 3/2014 |

OTHER PUBLICATIONS

International Search Report for PCT/EP2016/060355 by the European Patent Office, dated Jul. 15, 2016.
Written Opinion for PCT/EP2016/060355 by the European Patent Office, Jul. 15, 2016.

* cited by examiner

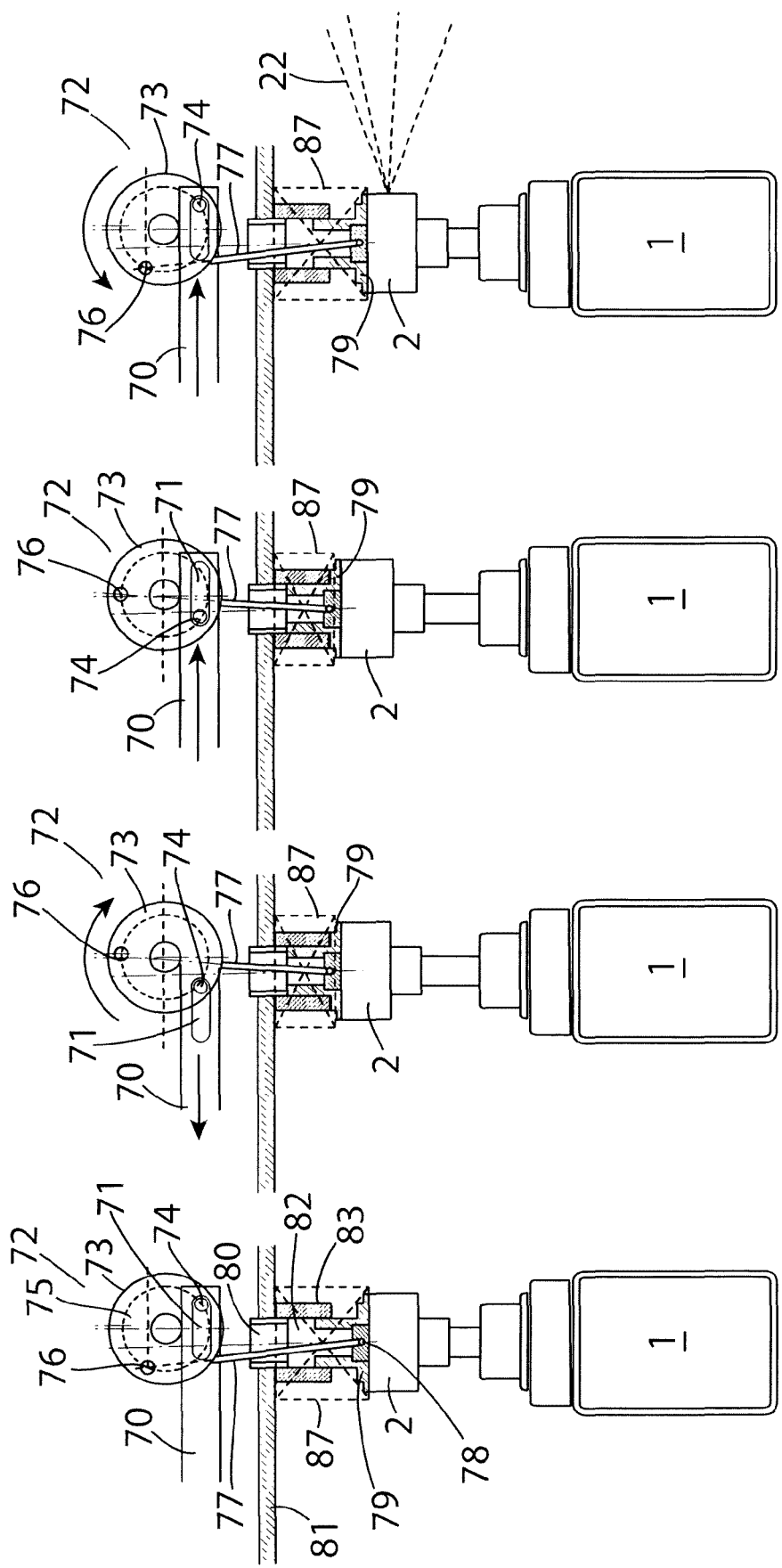

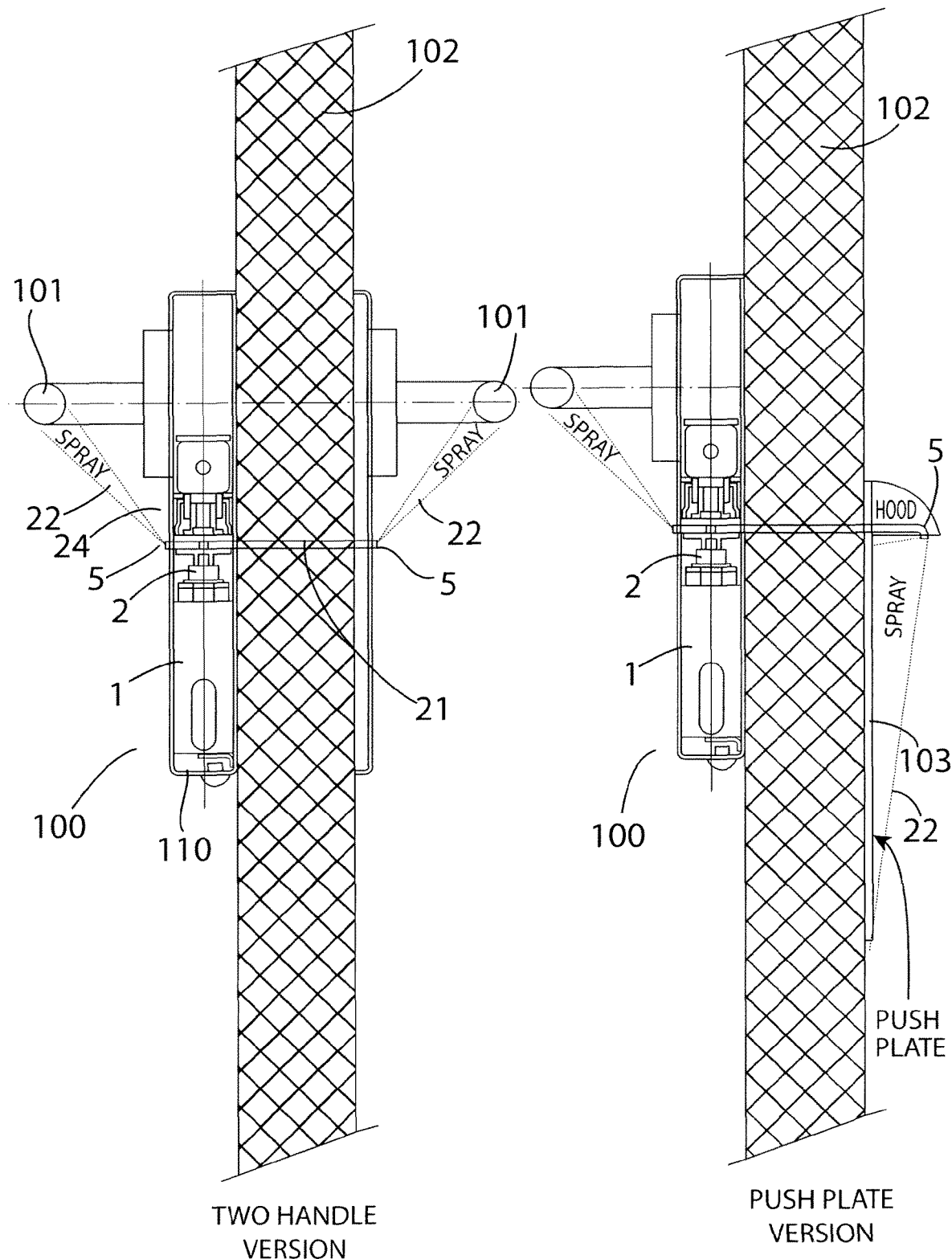

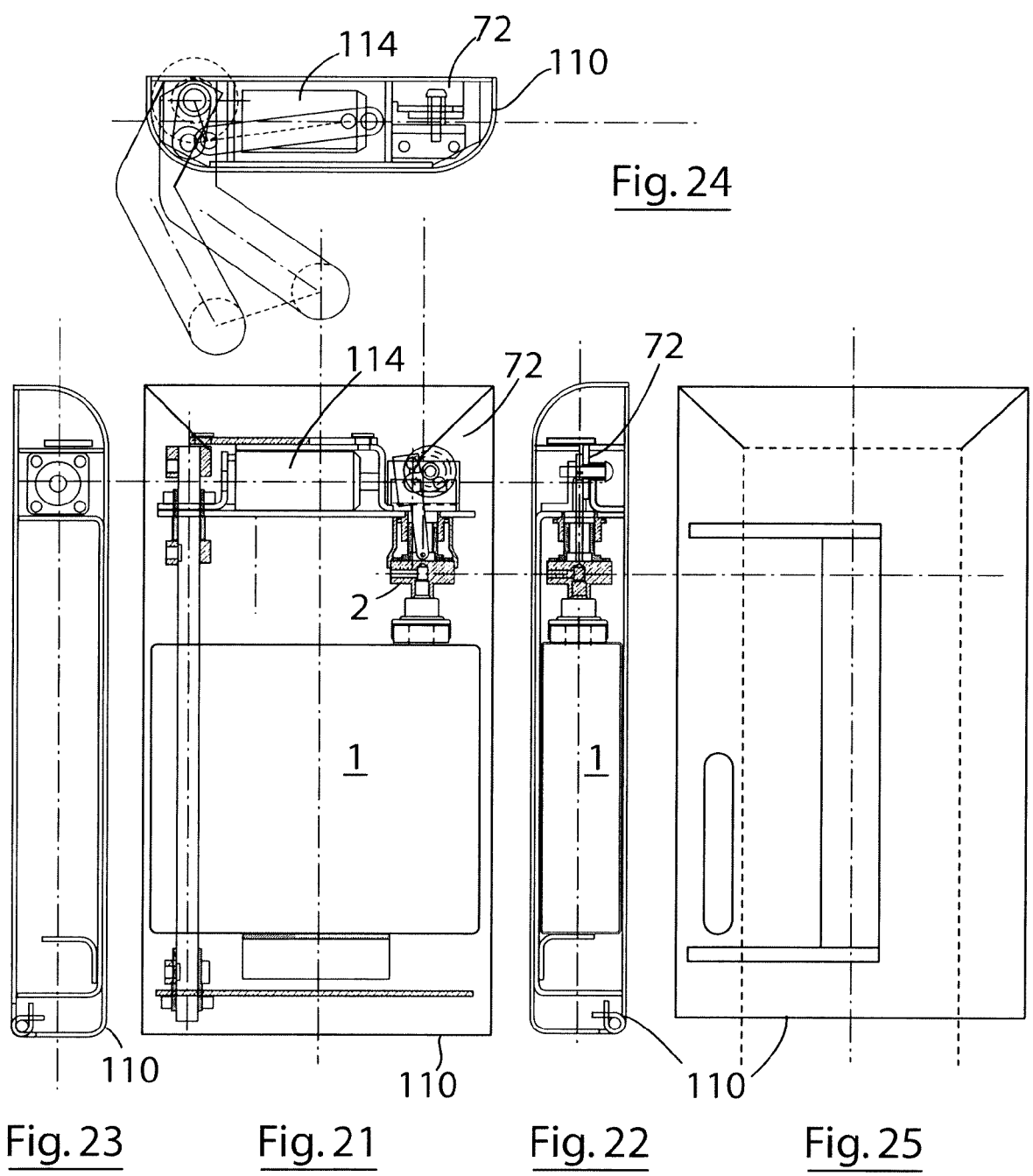

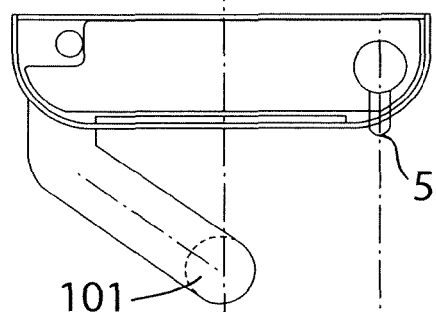
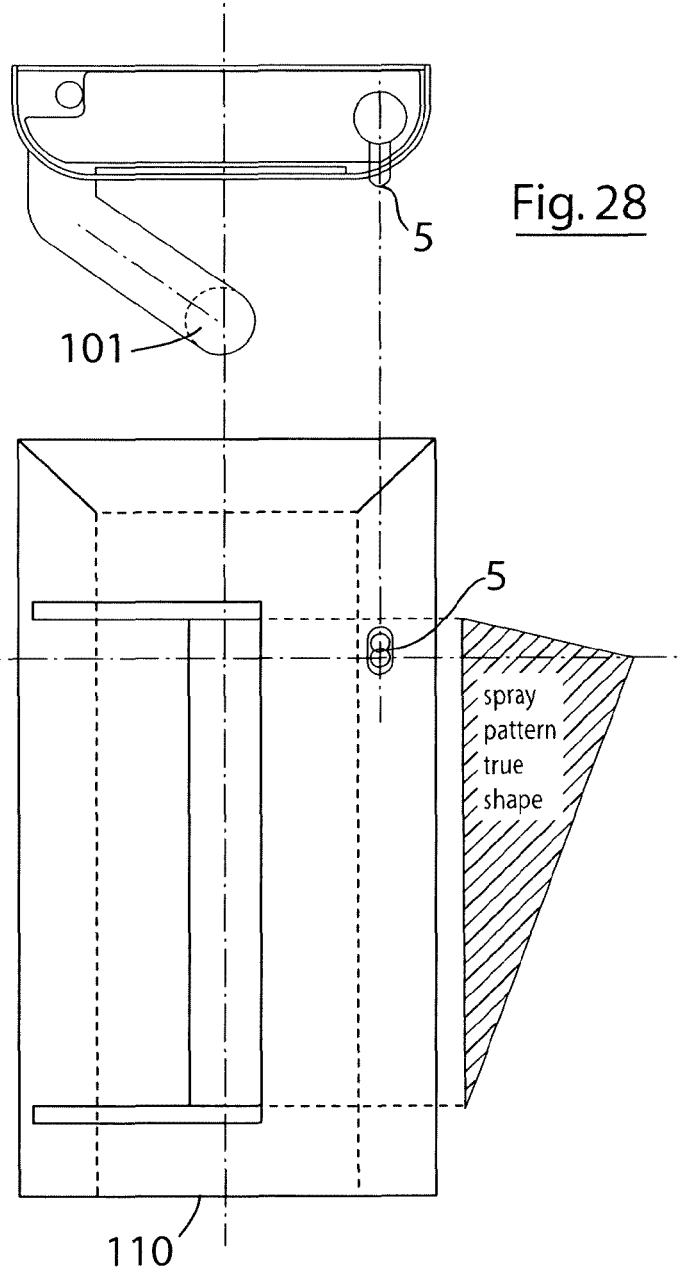
Fig. 28
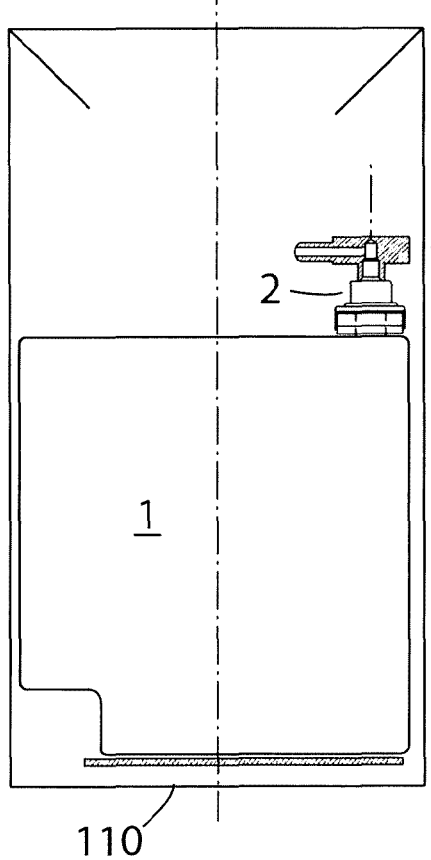
SPRAY PATTERN
VERTICAL HANDLE model
Fig. 27
Fig. 26

SANITIZER APPARATUS

CROSS REFERENCE TO RELATED APPLICATIONS

The present application claims priority to PCT Application No. PCT/EP2016/060355 filed May 9, 2016, which in turn claims priority to Irish Patent Application No. S2015/0141 filed May 7, 2015, both applications being incorporated in their entirety herein by reference thereto.

FEDERALLY SPONSORED RESEARCH AND DEVELOPMENT

None.

BACKGROUND OF THE INVENTION

1. Field of the Invention

This invention relates to a sanitizer apparatus for use with door handles.

2. Background

It has been well documented in the past that hard surfaces play a major role in the spread of bacteria. The door handle is one of the most commonly touched hard surfaces that is used day to day, especially the toilet door handle, and has been identified in many surveys as a contributor to people becoming sick.

It is an object of the present invention is to reduce or eliminate the door handle as a source of contamination.

SUMMARY OF THE INVENTION

According to the invention there is provided a door handle sanitizer apparatus, including a sanitizing fluid reservoir, an atomizing pump having an inlet connected to the sanitizing fluid reservoir and an outlet connected to a discharge spray head, atomizing pump actuating means, said atomizing pump actuating means being operatively connected to the door handle in use for operation in response to movement of the door handle.

In one embodiment of the invention the pump actuating means is mechanically operated.

In another embodiment the pump actuating means includes a primary time delay mechanism.

In another embodiment the primary time delay mechanism comprises an actuating rod or shaft which is movable in a first direction to prime the atomizing pump and is moveable in the opposite or second direction to operate the atomizing pump to eject a spray of sanitizing fluid from the reservoir, there being provided means for initially delaying or slowing movement of the shaft in said opposite direction for a pre-set time delay period.

In a further embodiment the shaft is biased into a normal rest position and a cam mechanism is connected to the door handle such that moving the door handle to an open position causes the cam to urge the shaft against bias in said first direction to prime the atomizing pump.

In another embodiment the delay mechanism comprises a damping mechanism.

In another embodiment said shaft is mounted on and is axially moveable through an associated fluid filled cylinder with outer ends of said shaft projecting outwardly of the cylinder, a piston mounted on the shaft within the cylinder, a bore of the cylinder having a first portion in which fluid within the cylinder moves freely past the piston and a second portion wherein the piston cooperates with the bore of the cylinder to restrict movement of fluid past the piston.

In another embodiment the piston has a fluid passage extending through the piston for substantially free movement of fluid through or past the piston, a floating seal mounted on the piston associated with said fluid passage, said seal being moveable between a disengaged position when the shaft moves in said first direction exposing said fluid passage for movement of fluid therethrough, and an engaged position when the shaft moves in said second direction for sealing engagement between the piston and a cylinder in the second portion of the cylinder thus blocking fluid movement through said fluid passage and leaving only a restricted fluid passageway between the piston and the shaft.

In a further embodiment, a secondary time delay mechanism is provided to prevent actuation of the atomizing pump until the delay means of the primary time delay mechanism is engaged.

In another embodiment the primary time delay mechanism is operatively connected to a bell crank device for actuation of the atomizing pump.

In another embodiment of the invention the bell crank device is movable between a neutral position and a cocked position which primes the atomizing pump, movement of the primary time delay device into the engaged position causing movement of the bell crank device into the cocked position.

In another embodiment of the invention the bell crank device locks in the cocked position when the primary time delay device is in the engaged position and the bell crank device is operated for movement into the neutral position by the primary time delay device when the primary time delay devices moves into the normal rest position.

In another embodiment of the invention the bell crank device comprises a rotatable disc connected to the primary time delay device for rotation of the disc about a central axis of the disc through an arc, an actuating rod connected by a first pivot pin to the disc for pivotal movement about an axis parallel to the central axis of the disc, said actuating rod being connected by a second pivot pin 2 to a spring-loaded pump actuating plate which engages the pump, rotation of the disc acting through the actuating rod to move the pump actuating plate between a pump priming position and a pump discharge position.

In another embodiment of the invention the first pivot pin is movable into an over-centre position in the cocked position to lock the bell crank device, the first pivot pin being movable out of the over-centre position in response to movement of the primary time delay mechanism out of the engaged position.

In another embodiment of the invention a cocking pin is provided for connection to the door handle such that operation of the door handle causes translational movement of the cocking pin to move the time delay mechanism into the engaged position.

In another embodiment of the invention as the cocking pin moves the time delay mechanism into the engaged position, it also moves the bell crank device into the cocked position.

In another embodiment of the invention the cocking pin has an elongate slot which engages a disc actuating pin projecting outwardly from a face of the disc, such as translational movement of the cocking pin causes rotational movement of the bell crank disc.

In another embodiment of the invention the time delay mechanism and the bell crank device are mounted on a support platform, the actuating shaft and cocking pin being movable parallel to the support platform, an elongate slot in the cocking pin engaging with a pin projecting outwardly from a face of the disc to rotate the disc, the bell crank actuating rod passing through an opening in the platform and through a cylindrical housing to engage the pump actuating plate which has a tubular spigot slidably engaged with the bore of the housing, a spring being mounted between the pump actuating plate and the housing or platform to urge the pump actuating plate away from the platform.

In another embodiment of the invention a cam on the door handle is engagable with the cocking pin for movement of the cocking pin.

In another embodiment of the invention a link arm is operably connected to the door handle, said link arm having an elongate slot for reception of the disc actuating pin, translational movement of the link arm causing rotational movement of the bell crank disc.

In another embodiment of the invention a secondary time delay mechanism is provided to prevent actuation of the atomizing pump until the delay means of the primary time delay mechanism is engaged.

In another embodiment of the invention the secondary time delay mechanism comprises a pendulum delay device.

In another embodiment of the invention the pendulum delay device comprises a pair of pendulum plates which swing on pivots, lower edges of the pendulum plates engaging and holding the pump in a discharge position until the primary time delay mechanism is in the engaged position, a plate on the shaft urging the pendulum plates apart when the primary time delay mechanism is in the engaged position allowing the pump to move into a primed position.

In another embodiment of the invention an activator cam is operable to move the shaft of the primary time delay mechanism between the normal rest position and the engaged position.

In another embodiment of the invention the actuator cam engages a roller rotatable mounted on a bracket connected to the shaft of the primary time delay mechanism for translational movement of the shaft.

In another embodiment of the invention a bleed screw communicates between a narrow portion of the bore of the cylinder and an exterior of the cylinder to control the rate of entry of air into the narrow portion of the bore of the cylinder.

In another embodiment of the invention the piston is formed by a cup seal mounted on the shaft.

In another embodiment of the invention the piston is axially movable on the shaft between spaced-apart stops, at least one port extending through the piston, a floating O-ring mounting in a circumferential channel in a side wall of the piston for movement between a disengaged position and an engaged position for sealing engagement between the piston and the narrow cylinder bore portion.

BRIEF DESCRIPTION OF THE DRAWINGS

The invention will be more clearly understood from the following description of some embodiments thereof, given by way of example only, with reference to the accompanying drawings.

FIGS. 6-9 are partially sectioned elevational views illustrating sequential steps in the operation of another door handle sanitizer apparatus according to the invention.

FIG. 10 is an elevational view showing a door handle sanitizer apparatus of the invention mounted on a door in one configuration of use.

FIG. 11 is a view similar to FIG. 10 showing the door handle sanitizer apparatus in another position of use.

FIG. 21 is a partially sectioned elevational view of another sanitizer apparatus according to the invention.

FIG. 22 is a side partially sectioned elevational view of the sanitizer apparatus shown in FIG. 21.

FIG. 23 is another side view of the sanitizer apparatus shown in FIG. 21.

FIG. 24 is a plan view of the sanitizer apparatus shown in FIG. 21.

FIG. 25 is a front elevational view of the sanitizer apparatus shown in FIG. 21.

FIG. 26 is a view similar to FIG. 25 showing another sanitizer apparatus.

FIG. 27 is a partially sectional detail elevational view of the sanitizer apparatus of FIG. 26.

FIG. 28 is a plan view of the sanitizer apparatus of FIG. 26.

DETAILED DESCRIPTION OF THE PREFERRED EMBODIMENTS

Figure 1:
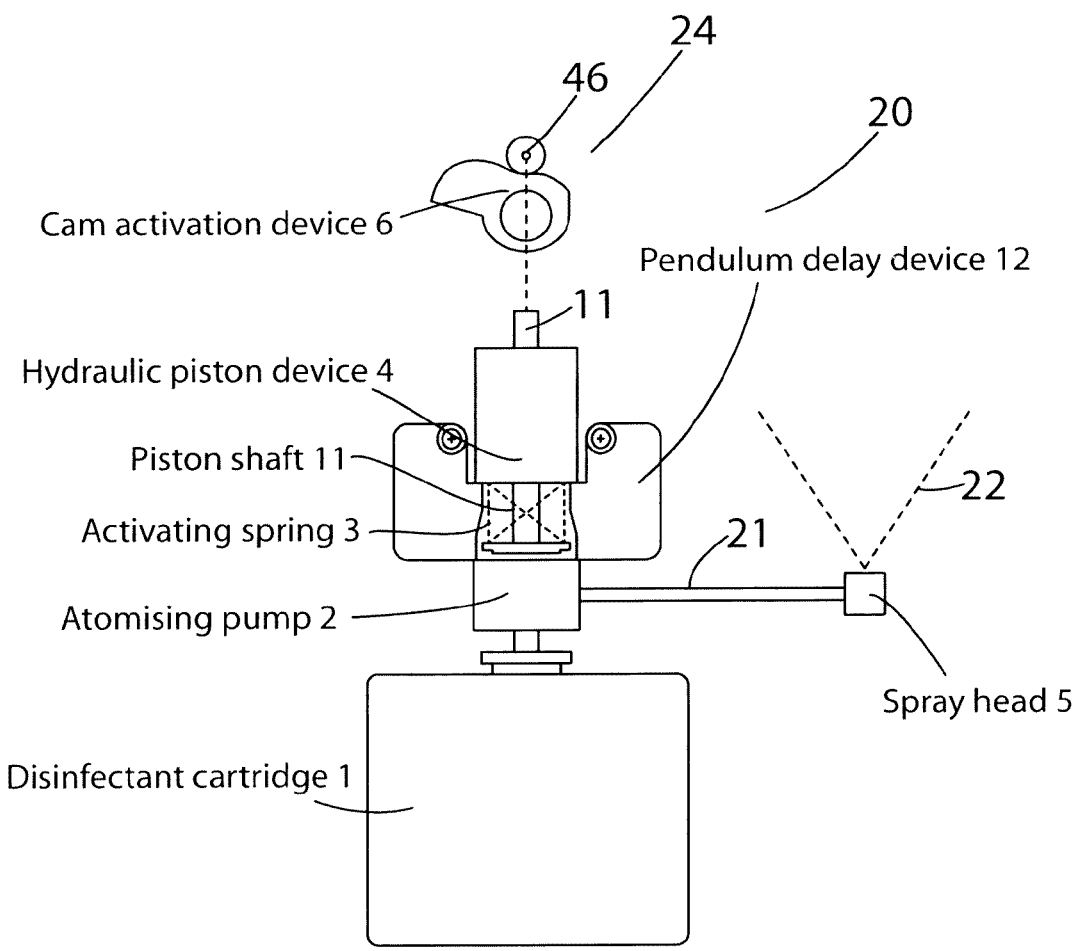
FIG. 1 is an elevational view illustrating a door handle sanitizer apparatus according to the invention.

Referring to the drawings, and in initially to FIGS. 1-3 thereof, there is illustrated a door handle sanitizer apparatus according to the invention indicated generally by the reference numeral 20. The apparatus 20 has a sanitizing fluid reservoir or disinfectant cartridge 1 and associated atomizing pump 2 having an inlet within the disinfectant cartridge 1 and an outlet connected by a pipe 21 with a spray head 5 for directing a sanitizing spray 22 at a handle of a door on which the apparatus 20 is mounted. Atomizing pump actuating means indicated generally by the reference numeral 24 is operatively connected to the door handle in use for operation of the atomizing pump 2 in response to movement of the door handle. The actuating means 24 incorporates a primary time delay mechanism in order to delay operation of the atomizing pump 2 so that the person opening the door will have removed their hand from the handle before spraying and the spray 22 will spray the handle rather than the person's hand.

Figure 2A:
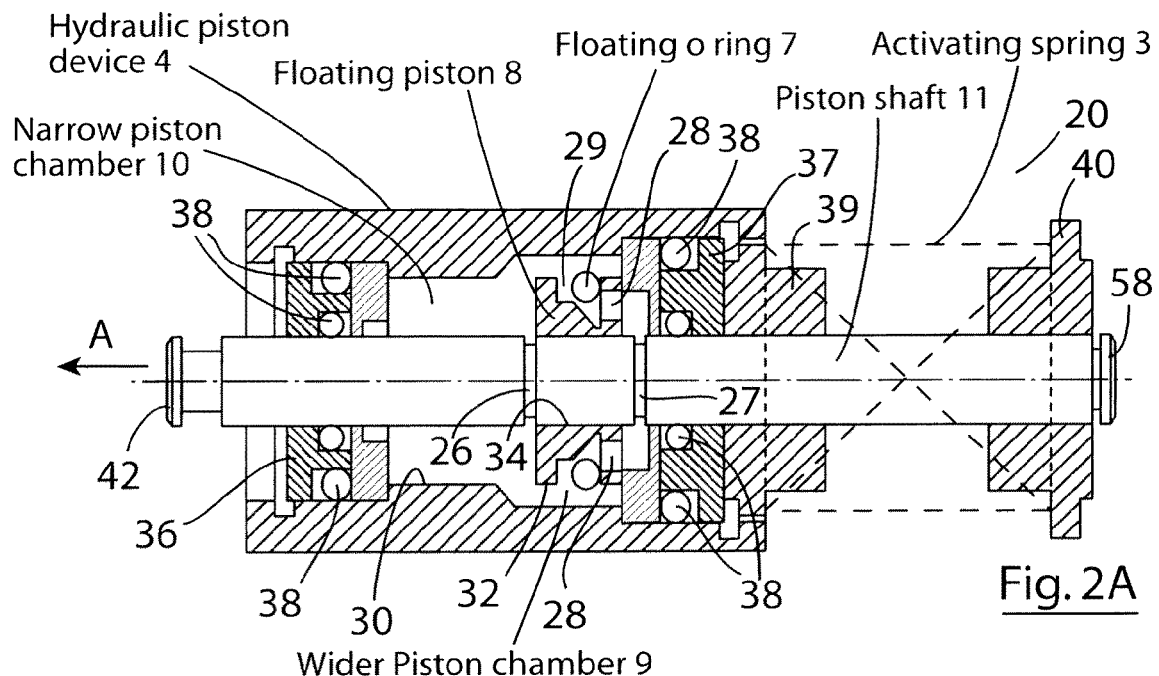
FIG. 2 shows sectional views illustrating portion of the sanitizer apparatus in different positions of use.
Figure 2B:
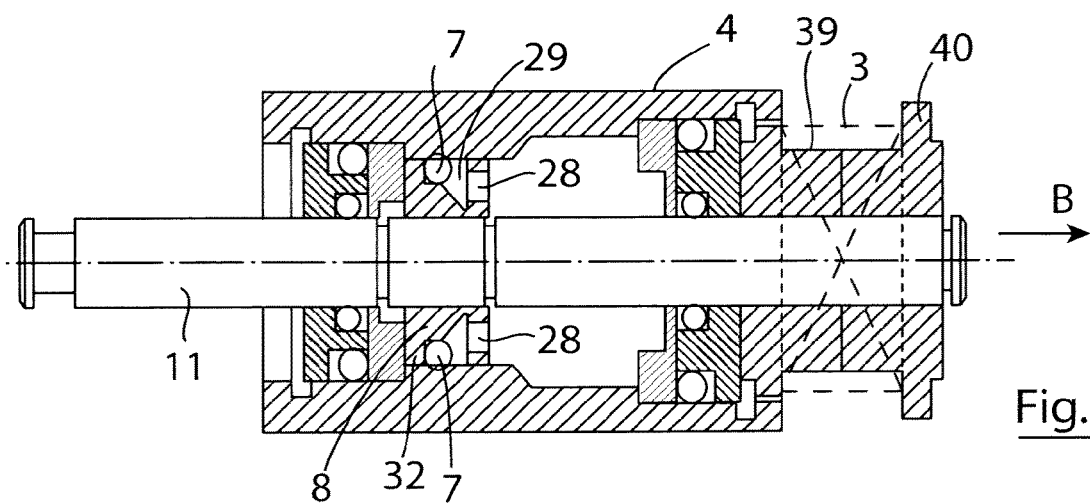

The actuating means 24 includes an actuating rod formed by a piston shaft 11 which is axially moveable through an associated fluid filled cylinder of a hydraulic piston device 4. A floating piston 8 is slidably mounted on the piston shaft 11 and is retained between circlips (not shown) which form spaced-apart stops and engage associated space-apart circlip mounting grooves 26, 27 on the piston shaft 11. A fluid passage 28 is provided by a number of ports or openings extending through the piston 8. A floating O-ring 7 is mounted within a circumferential channel 29 in a side wall of the piston 8 and is moveable between a disengaged position as shown in FIG. 2A when the piston shaft 11 moves in a first direction A exposing said fluid passage 28 for movement of fluid therethrough and an engaged position as shown in FIG. 2B when the piston shaft 11 moves in a second direction B for sealing engagement between the piston 8 and a narrow cylinder bore portion 30 of the hydraulic piston device 4 as shown in FIG. 2B. In this position the floating O-ring 7 engages against a flanged end 32 of the piston 8 at one end of the channel 29. Oil within the hydraulic piston device 4 can then only pass between an inner bore 34 of the piston 8 and an exterior of the piston shaft 11 on which it is mounted thus restricting oil transfer between the narrow piston chamber 10 and a wider piston chamber 9 portion of the interior of the hydraulic piston device 4 forming the fluid filled chamber.

The piston shaft 11 is slidably supported in end covers 36, 37 at opposite ends of the hydraulic piston device 4 with appropriate seals 38 between the end covers 36, 37 and the piston shaft 11 and internal bore of the hydraulic piston device 4. Spring mounting collars 39, 40 support an activating spring 3 at one end of the piston shaft 11.

Operation of the door handle causes the piston shaft 11 to move in a first direction A. Oil within the hydraulic piston device 4 can move freely past the piston 8 and the floating o-ring 7 is held in the disengaged position allowing movement of oil through the passages 28. Also while in the wider piston chamber 9, the oil can move around the exterior of the piston 8. When the piston shaft 11 moves in a second direction B opposite said first direction A, the floating O-ring 7 engages against the flange 32 and forms a seal between the piston 8 and narrow portion of the internal bore 30 of the hydraulic piston device 4. A small amount of oil will thus only bleed between the piston 8 and the piston shaft 11. Adjustment of the clearance therebetween will regulate the time delay before sufficient oil has moved past the piston 8 to allow it to move into the wider piston chamber 9 at which point the activating spring 3 snaps the piston shaft 11 downwardly operating the atomizing pump 2 to spray sanitizing fluid or disinfectant through the spray head 5.

Figures 3A, 3B:
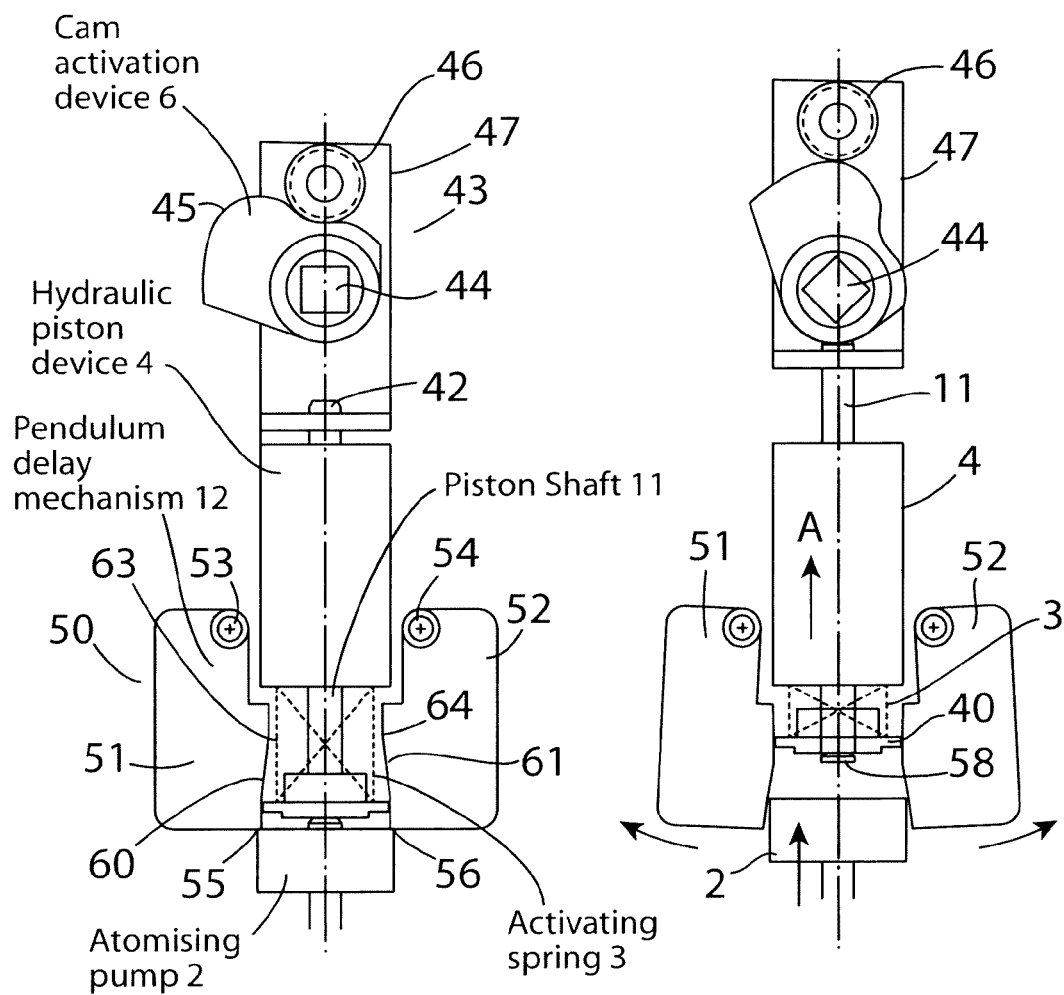
FIG. 3 shows elevational views illustrating the apparatus in different positions of use.

Referring in particular to FIGS. 3A-3B an upper end 42 of the piston shaft 11 is connected to a cam mechanism indicated generally by the reference numeral 43. The square section rotatable bar 44 of the door handle driveably engages a cam activation device 6 having an outer cam profile 45 which engages a roller 46 rotatably mounted on a bracket 47 to which the upper end 42 of the piston shaft 11 is attached. Moving the door handle into the opening position causes the cam activation device 6 to rotate pushing the roller 46 upwardly and raising the bracket 47 and hence the piston shaft 11, moving it in direction A as shown in FIG. 3B. This fully engages the time delay mechanism formed by the floating piston 8 which is now in the position shown in FIG. 2B.

To ensure the atomizing pump 2 does not discharge sanitizing liquid before the primary time delay mechanism is fully engaged, a secondary time delay mechanism indicated generally by the reference numeral 50 is also provided by a pendulum delay mechanism 12. The pendulum delay mechanism 12 comprises a pair of pendulum plates 51, 52 which swing on pivots 53, 54. Lower inner edges 55, 56 of these plates 51, 52 engage and hold the atomizing pump 2 in the downward discharge position until the cam activation device 6 has raised the piston shaft 11 sufficiently to engage the floating piston 8 in the narrow piston chamber 10 thus engaging the primary time delay mechanism. When the primary time delay mechanism has been fully engaged the spring collar 40 at a lower end 58 of the piston shaft 11 moves up tapered inner edges 60, 61 of the plates 51, 52 to a narrowed neck portion 63, 64 which when engaged by the spring collar 40 urges the plates 51, 52 apart as shown in FIG. 3B allowing the atomizing pump 2 to rise thus priming the atomizing pump 2. Thus when the piston shaft 11 subsequently moves downwardly in direction B of FIG. 2B it will engage and depress the atomizing pump 2 to discharge the disinfectant through the spray head 5 and at the same time reset the secondary time delay mechanism 50.

This invention is provided in versions to suit two commonly used door handle types. The operating mechanisms within each type however are identical.

Hydraulic Piston Device

This invention is a mechanical mechanism that is housed within a back and front cover plate for protection and the handle is then mounted on the front of the unit for operation. Firstly there is a hydraulic piston device mounted directly above the atomizing pump on a disinfectant cartridge. In between the hydraulic piston device and atomizing pump there is a spring mounted on the outside of the extended shaft of the piston device which is constantly pushing down from the hydraulic piston device towards the atomizing pump. The opposite end of this hydraulic piston device is attached to the door handle via a cam or cable which is bolted to the other end of the shaft.

When the handle is either turned or pulled in normal operation, the hydraulic piston device is also activated, travelling away from the spray head. The hydraulic piston device comprises of two stages of travel, one is free travel the second is delayed travel.

As the piston travels it transfers oil held within the cylinder from one side of the piston to the other side via a series of holes in the piston itself. There is a floating O ring or seal mounted on the piston in line with these holes and allows the oil to transfer one way but when the travel is reached the spring tries to reverse the travel by pulling the opposite direction towards the atomizing pump, this movement causes the floating O ring to move to the other side of it's seating on the piston and block the transfer of oil through the series of holes on the piston itself. Then the piston is separate to the shaft itself and is free to move being held by two circlips either side of it, the oil is then forced by the spring to divert around the outer diameter of the shaft and inner diameter of the piston. This diversion through a much smaller orifice gives a delayed travel and the length of delay is decided by the difference in size between the shaft and the piston. It is also possible to use a thicker oil to achieve a longer delay.

When the required delayed travel is achieved, free travel is desirable to push down on the atomizing pump so the inner cylinder diameter is increased, to allow the oil to travel freely around the outside of the piston, allowing the spring to pull down the piston to activate the atomizing pump.

Secondary Delay Mechanism for Atomizing Pump

It is desirable to avoid spraying the hands of a person if they do not fully turn or pull the door handle and thereby also not engage the time delay function of the hydraulic piston device. This invention also incorporates a mechanism to prevent this.

This mechanism stops the atomizing pump priming or moving until the second stage of delayed travel is reached within the hydraulic piston device. This comprises of a pendulum that has a taper on one side and is placed parallel to the piston shaft and spring. As the door handle is being activated and the piston is travelling away from the atomizing pump, the pendulum stops the atomizing pump from activating until the piston shaft has travelled through the free stage of travel and most of the delayed stage of travel. The shaft then reaches the end of the taper and moves the pendulums outwardly which release the atomizing pump, which moves outwardly to prime the atomizing pump, when the hydraulic piston device is well into the delayed travel stage, ensuring the full delay time will take place before the unit sprays the door handle. This mechanism is fitted to both the pull and turn type door handles.

The Pull Handle Version

The pull handle is usually installed with a door closer and does not have a door lock mechanism. The design of the pull handle incorporates two pivot arms bolted to the inside of the outer cover. These arms protrude through two slots in the outer cover and the main vertical handle is bolted to the arms. The vertical handle comprises an inner bar fixed to the arms and an outer sleeve which is free to move.

As the user pulls the handle they have to overcome the resistance of the weight of the door and the door closer providing enough energy to activate our hydraulic piston device which in turn activates the atomizing pump to clean the door handle. The design of the handle with two pivot points means that the mechanism is activated from any part of the handle ensuring it is activated every time.

The pivot points allow the main handle to move activating the hydraulic piston device, via a cam or cable which is attached to one of the lever arms of the door handle. The length of the arm also provides leverage to the user making it easier to activate. While the hydraulic piston device travel has been kept to a minimum, the handle must travel a much greater distance to make it easier to activate. The length of the arms can be increased to gain more leverage to overcome lighter doors or lighter door closers.

On the cable version a pulley wheel is installed and the cable is looped around it. When the pulley is attached to the handle arm and pulled you get the effect of halving the movement because the pulley moves the cable on both sides, whereas with the cam version the handle has to move a greater distance to activate the mechanism.

The Lever Handle Version

The lever handle usually has a lock installed with it and with normal operation the user turns the lever handle to open the lock. Our version appears and operates the same as a standard lever handle but with our mechanisms contained within a cover plate on which the handle is mounted. In our version, the same time as the lock is being opened, the hydraulic piston device is being activated via the cam or cable that is mounted on the square bar that goes between both handles and through the lock. As the square bar turns to open the lock, it moves the cam or cable, which starts the travel on the hydraulic piston device, resulting with the handle being sprayed with disinfectant after the delayed travel.

Handle Rotation

All our different handle types allow for rotation. We obtain handle rotation in different ways. One is natural rotation obtained from the user grabbing the rotating handle. Method two is to install a ratchet mechanism in line with the travel of the handle which results in the handle rotating. Method three is to manipulate the user to rotate the handle to gain extra function. This ensures that the whole surface area of the handle is constantly realigned for full exposure to the antibacterial spray. Each method is explained in detail in section 4.

FIG. 1 shows an overall schematic of assembled parts. This section gives the general layout of all internal parts contained within the unit, it also explains there basic function and the sequence of the operation.

FIG. 1 gives the layout of individual parts contained within the unit. From bottom to top we have the disinfectant cartridge 1 which contains the disinfectant fluid to be sprayed on handle.

Crimped or treaded to the top of disinfectant cartridge 1 is the atomizing pump 2 which when activated by the hydraulic piston device 4 pumps the fluid up to spray head 5 which in turn atomizes the fluid onto the handle.

Next we have the activating spring 3 placed between atomizing pump 2 and hydraulic piston device 4, mounted on the outside of piston shaft 11 which extends out the bottom of hydraulic piston device 4 and activates atomizing pump 2.

On the top of hydraulic piston device 4 we have the opposite end of piston shaft 11 connected to cam activating device 6 which in turn is mounted to the square bar that goes between the lock and two handles.

When the handle is turned in normal operation to open the door, it also pulls piston shaft 11 upwards the full required travel which is both our free travel and delayed travel. In achieving this travel, the atomizing pump 2 lifts up to prime via an internal spring and primes itself. Then activating spring 3 pulls down reversing this travel, it pulls down slowly through our delayed travel and then unrestricted pushes down on atomizing pump 2 the free travel which sends the fluid through to spray head 5 which atomizes the fluid onto the door handle.

This operation is the same in both the lever and pull type handles, only the activation from cam to pulley changes on the pull type handle to facilitate the vertical handle.

FIG. 2 shows a detailed schematic of the primary delay device. This section deals with the primary delay device described as 4, this is the mechanism that is activated by the handle, and then it controls all other functions and the sequence they activate in, including the delay time and the activating of the atomizing pump.

This drawing gives in detail the different stages of travel of part hydraulic piston device 4.

FIG. 2A shows hydraulic piston device 4 in a stand by position, where activating spring 3 is fully extended. Piston shaft 11 is fully extended downwards with floating piston 8 containing floating o ring 7 resting in the right hand side of wider piston chamber 9 with the oil contained on the left side.

FIG. 2B shows piston shaft 11 having travelled both the free and delayed travel to the opposite side of hydraulic piston device 4. With activating spring 3 fully compressed and piston shaft 11 protruding through the left side of hydraulic piston device 4 the full travel length. While floating piston 8, containing floating O-ring 7 is travelling, it is transferring the oil through a series of holes in floating piston 8 with floating piston 7 being positioned to allow this to happen.

Having freely transferred the oil from one side of itself to the other, it is now positioned in the left hand side of the narrow piston chamber 10. When activating spring 3 pulls piston shaft 11 in reverse floating O-ring 7 moves to the other side of its' seating which blocks the easy transfer of oil through the holes within floating piston 8. This in turn forces the oil through the outside of piston shaft 11 and through the inner diameter of floating piston 8, which has a much smaller orifice and delays the time it takes to transfer the oil.

Figure 2C:
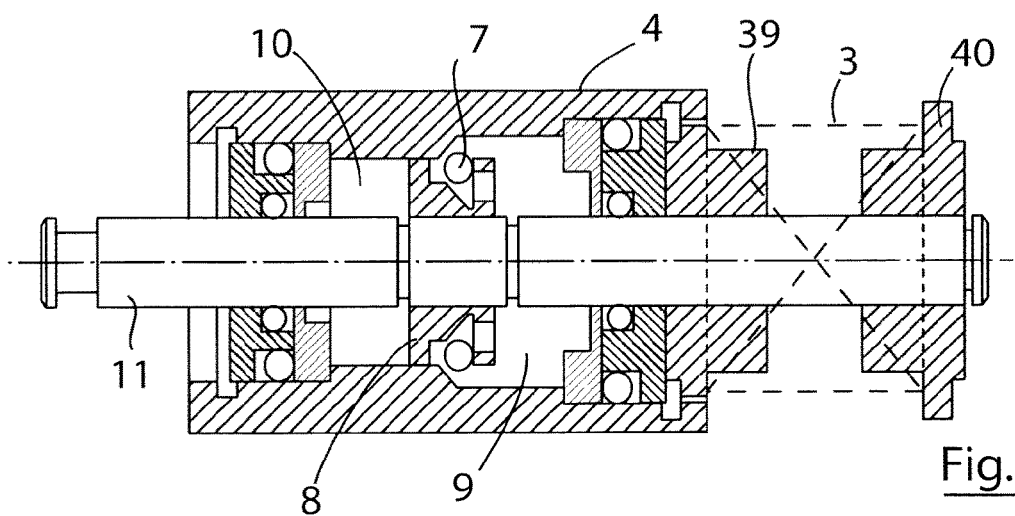

FIG. 2C shows piston shaft 11 at the end of its' restricted travel where it is just about to enter into wider piston chamber 9. Here it can freely push down the second free travel stage to activate atomizing pump 2 (which is not shown). This shows activating spring 3 in a half compressed state and piston shaft 11 protruding, just half its' travel, through the top of hydraulic piston device 4.

FIG. 3 shows a detailed schematic of the secondary delay device. This secondary delay device 50 is used to ensure that the atomizing pump 2 cannot activate until the primary hydraulic delay mechanism has travelled through the free travel and into the delayed travel. This protects against premature activating of the atomizing pump 2 which can happen on the lever type handle especially when the user is entering a room and closing the door behind them. At the point of closing some users do not push the lever down all the way as they are only entering the lock into the door frame slot with an open door. But when opening the door the user must push down the full way to release the lock from the door frame slot.

FIG. 3A shows cam activating device 6 in standby, with piston shaft 11 connected to the bottom, protruding from the top of hydraulic piston device 4. The bottom side of hydraulic piston device 4 shows piston shaft 11 extending downwards with activating spring 3 fully extended on the outside of it. Then we have pendulum delay mechanism 12 mounted with the taper side parallel to activating spring 3 and sitting on top of atomizing pump 2 preventing it from moving.

FIG. 3B shows cam activating device 6 in an activated state with piston shaft 11 protruding the full travel length, through the top of hydraulic piston device 4. Then on the bottom side of hydraulic piston device 4, it shows activating spring 3 in a compressed state, with the end cap of piston shaft 11 having travelled the length of the taper on pendulum delay mechanism 12. This moves pendulum delay mechanism 12 out of the way of atomizing pump 2 to allow its' internal spring to push it upwards to prime.

FIG. 4 shows the detailed description of handle rotation.

This section deals with the multiple ways of handle rotation; 1, by natural rotation via standard operation of the handle, or 2, by a ratchet mechanism placed in line with the handle travel, or 3, by user manipulation to rotate handle to achieve extra function.

There are two main types of lever handles available one is called a passive set, usually used for rooms where privacy is not an issue, this has a latch but is not lockable. The second type is called a privacy set, used where privacy is required and is lockable on one side. We have taken both types and installed rotational devices to both as described below.

Our lever handle, 13, for rotational purposes, differs from standard lever type handles which are usually moulded to the stem. The stem is attached to the door via a mounting plate with a square bar which opens the lock inside the stem. We have detached the lever handle from the stem and attached an inner rod fixed to the stem with an outer sleeve over the rod, which is now the lever, and free to rotate. On some versions we have rotations on both sides of the stem, joined internally either side of the stem for simultaneous dual rotation.

FIG. 4—this version relates to the passive lever handle.

Figure 4A:
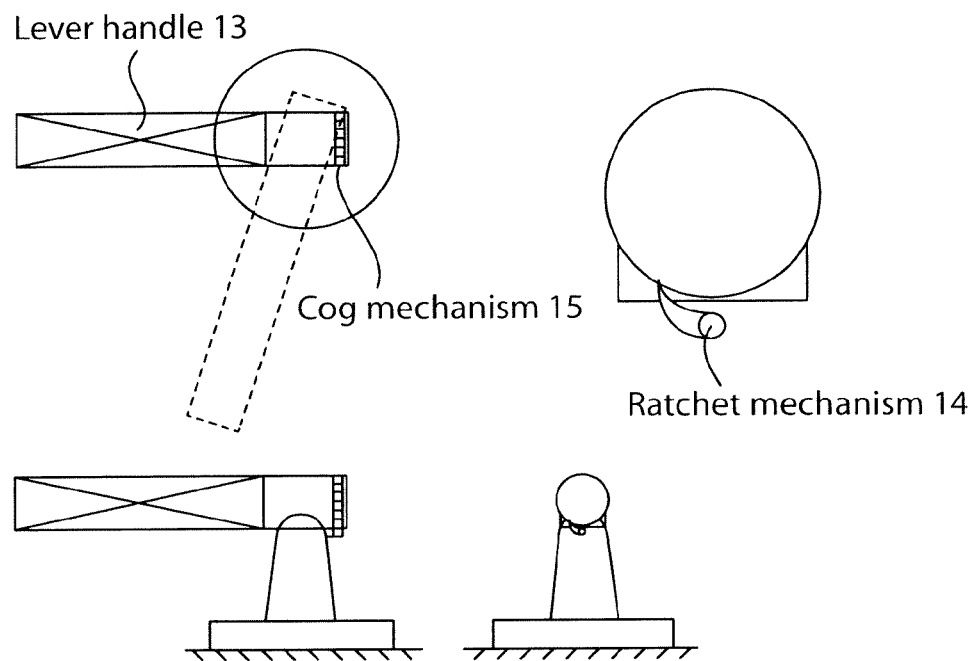
FIG. 4 shows various views of portions of sanitizer apparatus according to the invention.

FIG. 4A shows lever handle 13 in an idle position waiting for use. Next it shows the direction of travel via the arrow when activated. As the user is pushing lever handle 13 all the way down in normal operation, to open the lock, we have placed, on the opposite end of lever handle 13, on the other side of the stem, a small series of cogs which have to pass through ratchet mechanism 14 in normal operation to open the lock. They pass through ratchet mechanism 14 freely as it has a one way mechanism built in to allow this to happen but when it is in reverse travel returning to idle position ratchet mechanism 14 blocks this travel and makes lever handle 13 rotate to pass through. The cog mechanism can also be changed for a rubber sleeve which will cause friction and rotate when passing through ratchet mechanism 14.

Figure 4B:
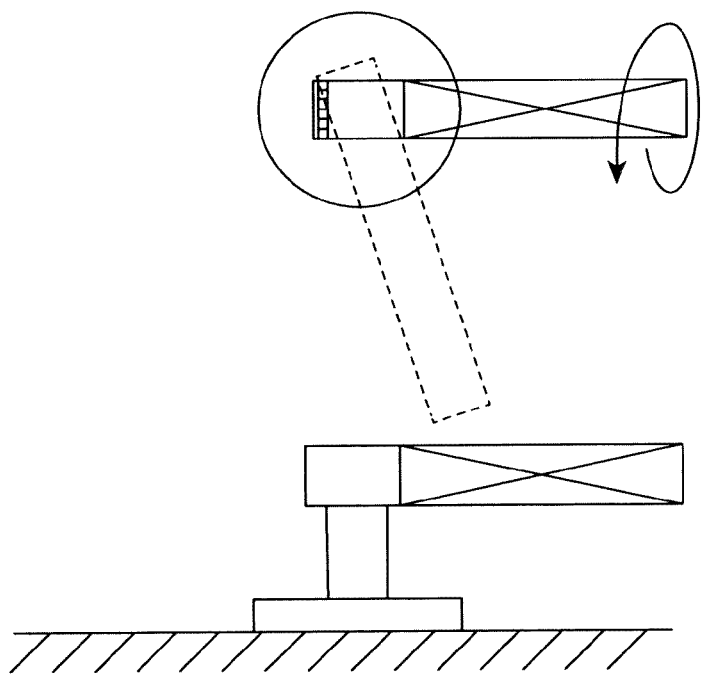

FIG. 4B this version relates to natural rotation.

FIG. 4B shows lever handle 13 in an idle position with the direction of travel indicated by the arrow. When lever handle 13 is in normal operation, to open the lock, the user pushes downwards and the lever is rotated by this action.

Figure 4C:
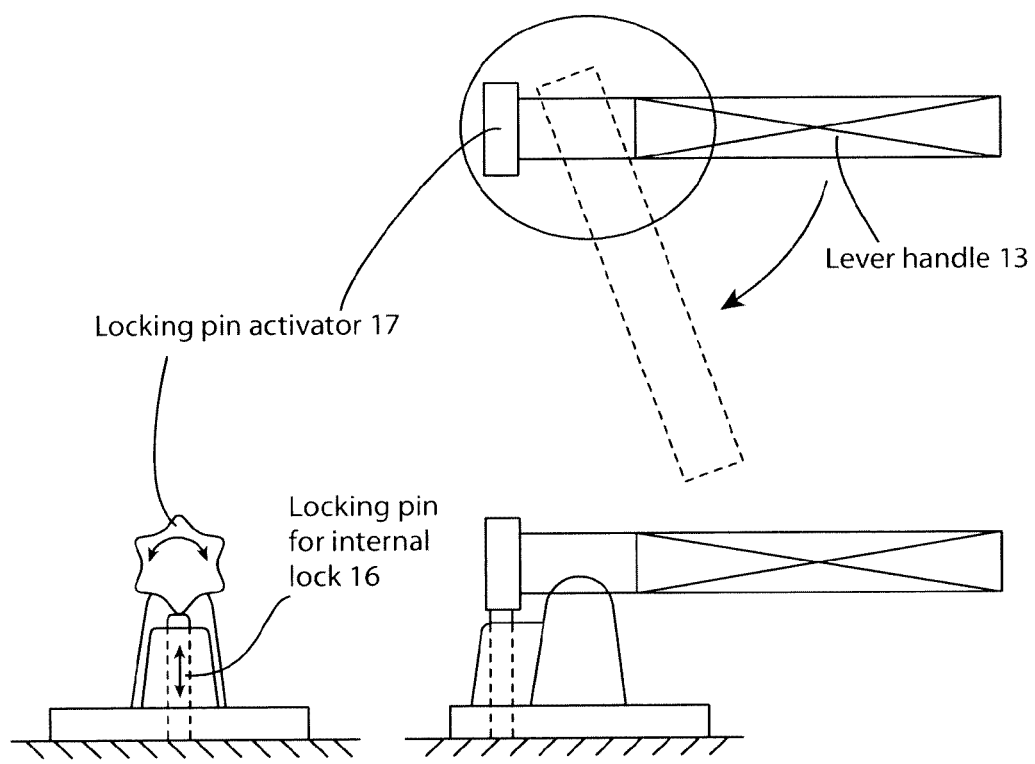

FIG. 4C—this version relates to the privacy lever handle.

FIG. 4C shows lever handle 13 with the handle lever on the right of the stem for the hand to operate the lock. On the opposite of the stem it shows locking pin activator 17 which is attached to the hand lever through the stem and rotates with lever handle 13 as one. When the user wants to lock the door for privacy, they must rotate the handle which in turn rotates locking pin activator 17 on the far side of the stem. This is circular in shape with high points. When one of the high points passes locking pin 16, it pushes locking pin 16 inwards to lock the door. This turning of the lever to lock the door assures rotation every time the user locks the door for privacy.

Vertical Pull Type Handle

This handle is mounted on a door with no lock and usually has a door closer fitted as well. This handle also contains an inner locked shaft and an outer free to move sleeve. The way we gain rotation on this handle is as follows: when the person pulls the handle to open the door, at the same time as they are activating our delay mechanism, they are also pulling the door open, most times a full 90 degrees. This pulling motion gives us rotation because the unit travels on the same arc as the door because it is fixed to it. The operator holds the rotating outer sleeve of the handle to pull the door open and it is this action of the door and unit moving on the same arc, while the outer sleeve is held in the operators' hand and it is this holding of the outer sleeve that causes the rotation every time the handle is pulled.

FIG. 5—this section shows how it is possible to achieve spray coverage of both handles on the same door with only one mechanism. This can be achieved in two ways, either by having a second spray pump side by side with the first one in the cartridge. This is connected via a tube to a second spray which is mounted on the other side of the door, in line with the lever on the door handle. The two atomizing pumps are activated simultaneously by the same mechanism. The second method is to use a larger volume atomizing pump and tee off this larger pump to both spray heads on either side of the door.

Figure 5A:
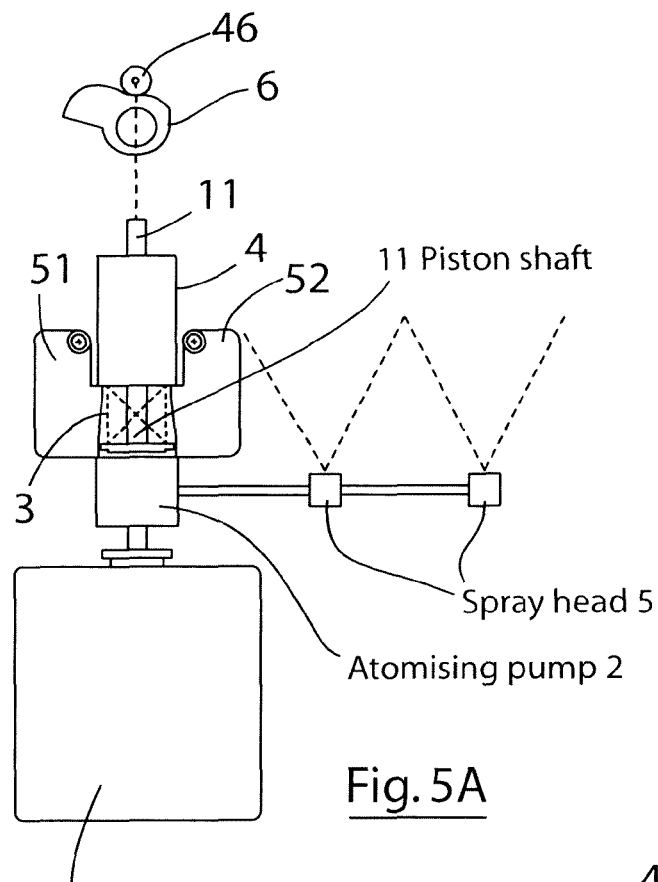
FIG. 5A is an elevational view of a door handle sanitizer apparatus according to another embodiment.

FIG. 5A is similar to the drawing marked FIG. 1 where all the working parts are explained. The main differences in the two drawings are that FIG. 5 has a larger disinfectant cartridge 1 and a larger atomizing pump 2 which is capable of feeding two spray heads 5.

Figure 5B:
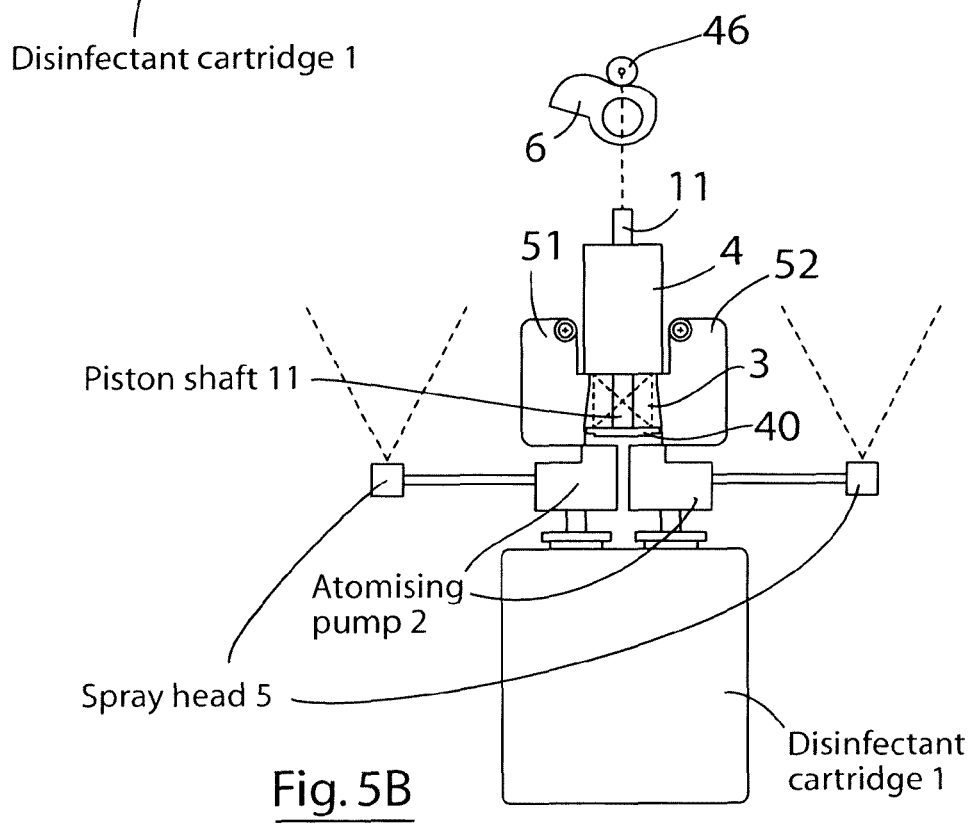
FIG. 5B is an elevational view of a door handle sanitizer apparatus according to further embodiment of the invention.
Figures 12, 13:
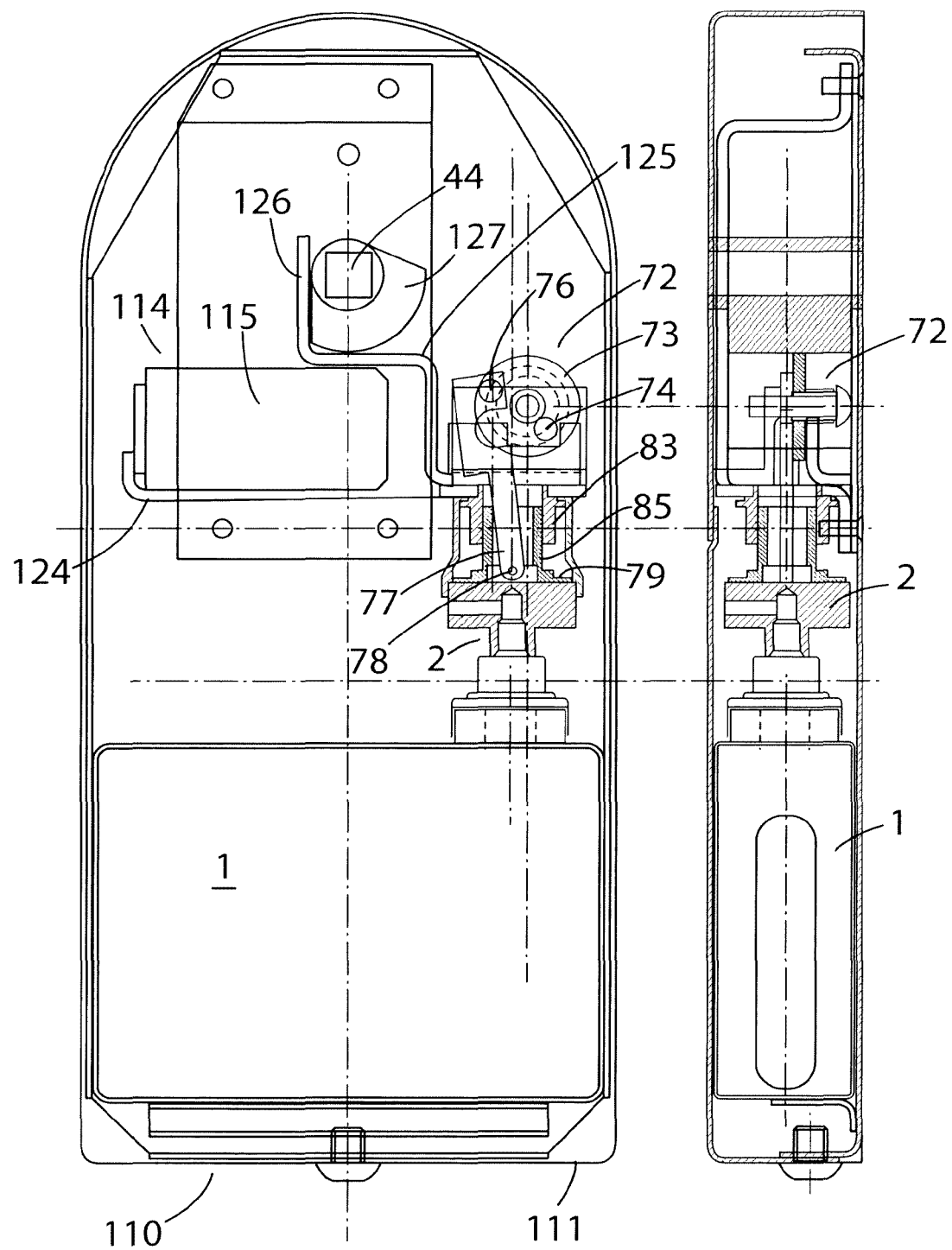
FIG. 12 is a partially sectioned elevational view of another sanitizer apparatus according to the invention.
FIG. 13 is a side, partially sectioned elevational view of the sanitizer apparatus shown in FIG. 12.

FIG. 5B—in this diagram we have mounted a second atomizing pump 2 side by side with the first one. This way the two atomizing pumps 2 are independent of each other and supply a spray head 5 each. The end cap 40 of piston shaft 11 is enlarged to accommodate the activating of the second atomizing pump 2.

FIGS. 6-9 show a revised mechanism according to another embodiment of the invention for actuating the spray head. A link arm 70 has an inner end operatively connected to the shaft 11 of the primary time delay mechanism. The link arm 70 has an elongate slot 71 adjacent an outer end thereof. A bell crank 72 comprises a rotatable disc 73 having a laterally extending pin 74 projecting outwardly from a front face 75 of the disc 73, which pin 74 slidably engages in the slot 71. A pump actuating rod 77 has an upper end attached by pivot pin 76 to a rear face of the disc 73, and a lower end connected by a pivot pin 78 to a pump actuating plate 79 which engages the top of the pump 2. The actuating rod 77 passes through an opening 80 in a mounting bracket 81 and through a bore 82 of a cylindrical housing 83 depending from the mounting bracket 81 beneath the opening 80. A central upstanding cylindrical spigot 85 on an upper face of the pump actuating plate 79 is slidably engaged within the bore 82. A spring 87 mounted between the pump actuating plate 79 and the mounting bracket 81 about the housing 83 urges the pump actuating plate 78 downwardly, the movement of said pump actuating plate 79 being constrained by the pump actuating rod 77.

In operation, operation of the door handle causes the link arm 70 to move to the left (as shown in FIG. 7) at the same time engaging the primary time delay mechanism. This movement of the link arm 70 pulls the pin 74 in the same direction as the link arm 70 rotating the bell crank disc 73 clockwise (as shown in FIG. 7). This in turn pulls the pump actuating rod 77 upwardly compressing the spring 87 and priming the pump 2. It will be noted that the pivot pin 76 stops at a slightly over-centre position thus locking the actuating rod 77, spring 87 and pump actuating plate 79 in the raised position. As the primary time delay mechanism releases the piston shaft 11 will push the link arm 70 to the right (as shown in FIGS. 8-9). Once the pin 74 has travelled to the opposite side of the slot 71 the link arm 70 pushes the pin 74 in reverse, rotating the bell crank disc 73 counter-clockwise (as shown in FIGS. 8-9) which will move the pivot pin 76 in reverse and once it passes top dead centre, the spring 87 then snaps the pump actuating plate 79 downwardly (as shown in 9) to discharge the sanitizing spray 22 from the pump 2 towards the door handle.

FIG. 10 shows a sanitizer apparatus according to the invention indicated generally by the reference numeral 100 mounted adjacent handles 101 on a door 102 for spraying disinfectant from the sanitizing fluid reservoir 1 onto the handles 101. Parts similar to those described previously are assigned the same reference numerals. In this case spray heads 5 are provided at opposite sides of the door 102 for spraying disinfectant spray onto the handles 101 at opposite sides of the door 102.

FIG. 11 shows a generally similar arrangement, however in this case only a single handle 101 is provided on one side of the door and a push plate 103 is provided on the opposite side of the door. In this case then one of the spray heads 5 is adapted to direct a spray 22 of disinfectant fluid on to the push plate 103.

Referring now to FIGS. 12-20, there is shown another sanitizer apparatus according to a further embodiment of the invention, indicated generally by the reference numeral 110. Parts similar to those described previously are assigned the same reference numerals. In this case a primary time delay mechanism 114 is provided comprising a cylinder 115 having a stepped internal bore with a wide bore portion 116 and a narrow bore portion 117. A bleed screw 118 communicates between an exterior of the cylinder 115 and the narrow bore portion 117 to control the rate of entry of air into the narrow bore portion 117 of the cylinder 115. A piston is movable through the internal bore of the cylinder 115 and in this case the piston comprises a cup seal 120. A compression spring 121 is mounted about the shaft 11 inside a housing 122 that fits within the cylinder 115 and is retained on the shaft by a circlip 123. The time delay mechanism 114 and an associated bell crank device 72 are mounted on a support platform 124. A cocking pin 125 has an upper portion 126 engaged by a cam 127 mounted on the rotatable bar 44 of the door handles 101. A lower portion 128 of the cocking pin 125 is slidable across the platform 124 in a translational movement. In this case an open elongate slot 71 is provided in the lower portion 128 for reception and engagement with the pin 74 on the disc 73 of the bell crank 72.

Figure 14:
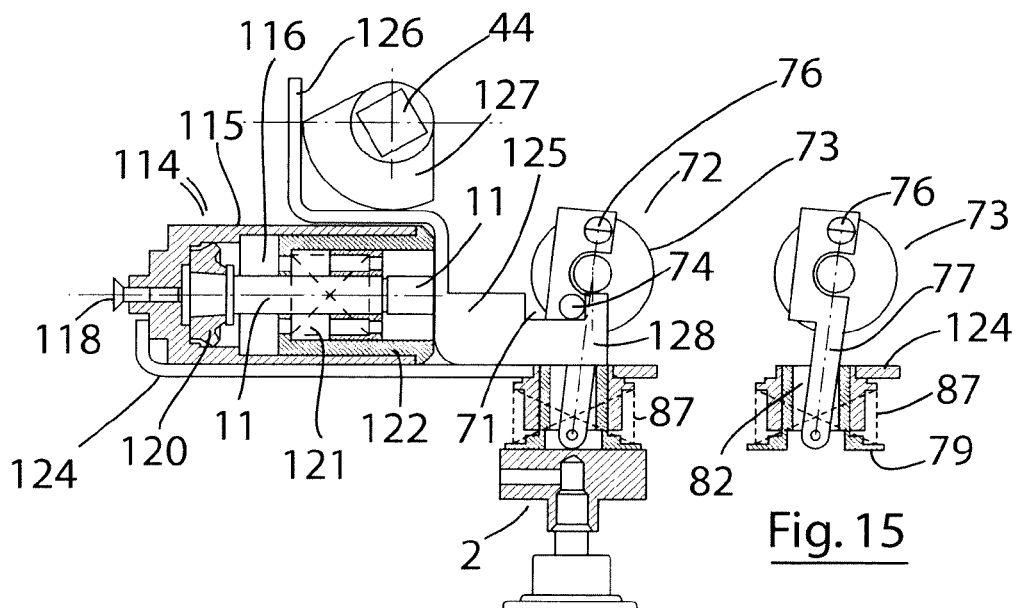
FIG. 14 is a detail, partially sectioned, elevational view showing portion of the sanitizer apparatus of FIG. 12.
Figure 15:
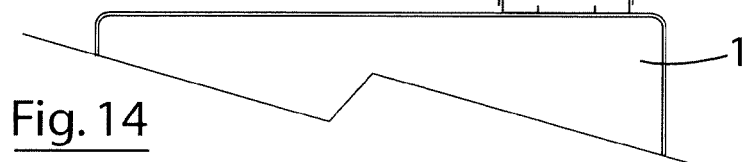
FIG. 15 is a detail view showing portion of the sanitizer apparatus of FIG. 12 in another position of use.
Figure 16:
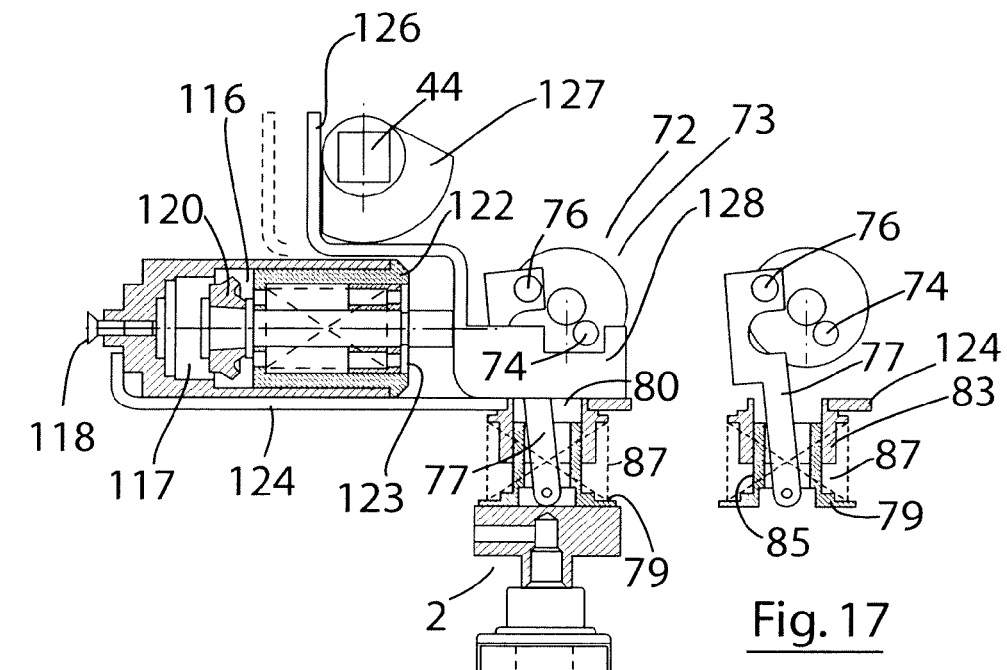
FIG. 16 is a view similar to FIG. 14 showing the sanitizer apparatus in another position of use.
Figure 17:
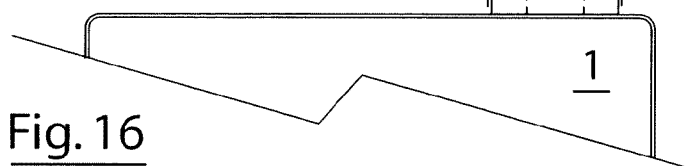
FIG. 17 is a detail view showing a bell crank device of the apparatus in another position of use.
Figure 18:
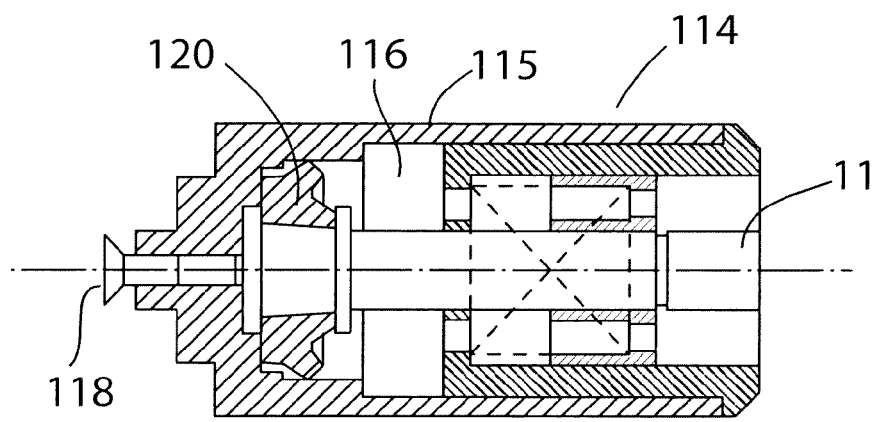
FIG. 18 is a detail sectional elevational view of a primary time delay mechanism forming portion of the sanitizer apparatus of FIG. 12.
Figure 19:
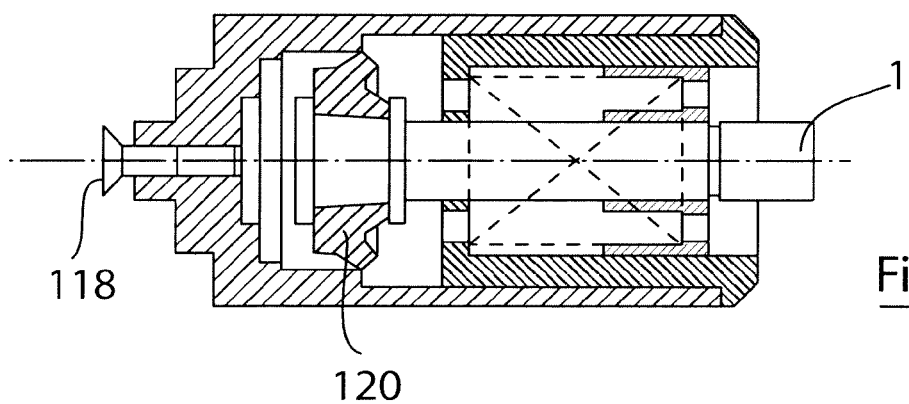
FIG. 19 is a view similar to FIG. 18 showing the primary time delay mechanism in another position of use.
Figure 20:
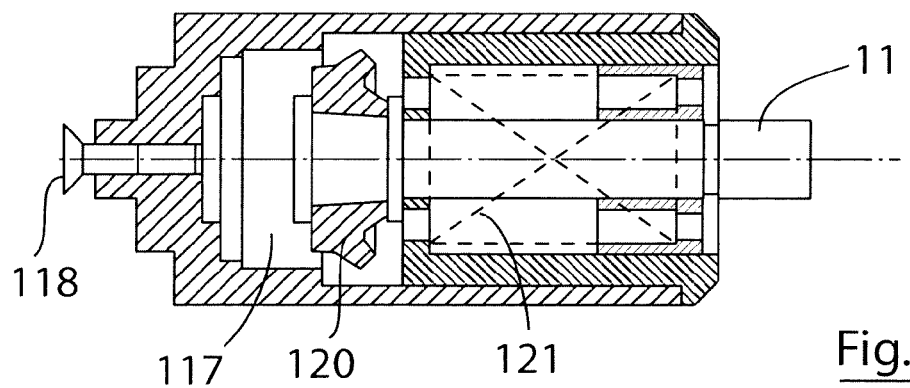
FIG. 20 is a view similar to FIG. 18 showing the primary time delay mechanism in a further position of use.

In a neutral or disengaged position the cup seal 120 locates in the wide bore portion 116 of the cylinder 115 and air flows freely past the cup seal 120. Upon rotation of the door handle, the bar 44 rotates the cam 127 to urge the cocking pin 125 to the left as shown in FIG. 14 urging the shaft 11 to the left and pushing the cap seal 120 into the narrow bore portion 117. As the cup seal 120 has a taper this allows the air to escape from the narrow bore portion 117 past the cup seal 120. When a door handle is released the spring 121 tends to urge the shaft 11 in the opposite direction however, travel of the shaft 11 is restricted because of the bleed screw 118 which limits the ingress of air into the narrow bore portion 117. As air is gradually allowed into the narrow bore portion 117, the shaft 11 gradually moves to the right as shown in the drawings until it reaches the wide bore portion 116 where it is then free and the spring snaps the shaft 11 to the right. As the cocking pin 125 moves to the left and the delay mechanism engages, the slot 71 moves the pin 74 of the bell crank 72 in a clockwise direction and hence the pin 76 into the over centre position as described previously in which the actuating rod 77 moves upwardly allowing the pump 2 to prime. As the cup seal 120 moves into the wide bore section 116, the shaft 11 pushes the cocking pin 125 to the right, thus urging the pin 74 in a counter-clockwise direction and moving the pin 76 back over centre to release the actuating rod 77 and the spring 87 urges the plate 79 downwardly to operate the pump to eject a spray of disinfectant from the reservoir 1.

FIGS. 21-28 show versions of the sanitizer apparatus adapted for a pull-handle type door, however, it will be appreciated that the time delay mechanism and bell crank device operation is essentially the same as for the previously described embodiments.

The purpose of this mechanism is to reduce the force requirements to actuate the spray head when minimal force input is available via door closer of other mechanism. This mechanism is primarily for the pull type door handle.

FIG. 6 shows the spray head in the unprimed rest position with spray head depressed and spring relaxed.

Linkage form actuator is at furthest point of travel left to right.

FIG. 7—handle has been pulled and actuator primed moving the linkage from right to left.

This motion rotates the bellcrank clockwise lifting the shaft, compressing the spring and thus allowing the spray head to prime.

The mechanism remains in this position until door handle is released by user.

FIG. 8—the delay mechanism begins to release and the linkage travels within the slot from left to right. The distance travelled here is in direct proportion to the delay time before the slot engages the bellcrank, and can be altered.

FIG. 9—delay mechanism has travelled to its furthest point left to right and the bellcrank has rotated anticlockwise releasing the tensioned spring and causing the piston to depress the spray head and release disinfectant fluid.

At the end of this motion we are in the status of FIG. 6 again.

By using the energy supplied by the user in operating the handle to activate our mechanism, which then sprays the handle with disinfectant every time the handle is used, this reduces greatly any germs left on the handle by previous users.

The terms "comprise" and "include", and any variations thereof required for grammatical reasons, are to be considered as interchangeable and accorded the widest possible interpretation.

The invention is not limited to the embodiments hereinbefore described which may be varied in both construction and detail within the scope of the appended claims.

What is claimed is:

1. A sanitizer apparatus for a door handle, including a sanitizing fluid reservoir, an atomizing pump having an inlet connected to the sanitizing fluid reservoir and an outlet connected to a discharge spray head, an atomizing pump actuating means being operatively connected to the door handle in use for operation in response to movement of the door handle, the atomizing pump actuating means including a primary time delay mechanism which is movable between a normal rest position and an engaged position in which operation of the atomizing pump actuating means is temporarily delayed, the primary time delay mechanism comprising an actuating rod or shaft which is movable in a first direction to prime the atomizing pump and is moveable in an opposite or second direction to operate the atomizing pump to eject a spray of sanitizing fluid from the sanitizing fluid reservoir, a damper for initially delaying or slowing movement of the actuating rod or shaft in said opposite or second direction for a pre-set time delay period, wherein the actuating rod or shaft is mounted on and is axially moveable through an associated fluid filled cylinder with an outer end of the actuating rod or shaft projecting outwardly of the associated fluid filled cylinder, a piston mounted on the actuating rod or shaft within the associated fluid filled cylinder, a bore of the associated fluid filled cylinder having a wide first portion in which fluid within the associated fluid filled cylinder moves freely past the piston and a narrow second portion wherein the piston cooperates with the bore of the associated fluid filled cylinder to restrict movement of fluid past the piston.

2. The sanitizer apparatus as claimed in claim 1, wherein the actuating rod or shaft is biased into the normal rest position and an operating mechanism is connected to the door handle such that moving the door handle to an open position causes the operating mechanism to urge the actuating rod or shaft against bias in said first direction to prime the atomizing pump.

3. The sanitizer apparatus as claimed in claim 1, wherein the piston has a fluid passage extending through the piston for substantially free movement of fluid through or past the piston, a floating seal mounted on the piston associated with said fluid passage, said floating seal being moveable between a disengaged position when the actuating rod or shaft moves in said first direction exposing said fluid passage for movement of fluid therethrough, and an engaged position when the actuating rod or shaft moves in said opposite or second direction for sealing engagement between the piston and the bore of the associated fluid filled cylinder in the narrow second portion of the associated fluid filled cylinder thus blocking fluid movement through said fluid passage and leaving only a restricted fluid passageway between the piston and the actuating rod or shaft.

4. The sanitizer apparatus as claimed in claim 1, wherein the primary time delay mechanism is operatively connected to a bell crank device for actuation of the atomizing pump.

5. The sanitizer apparatus as claimed in claim 4, wherein the bell crank device is movable between a neutral position and a cocked position which primes the atomizing pump, movement of the primary time delay device into the engaged position causing movement of the bell crank device into the cocked position.

6. The sanitizer apparatus as claimed in claim 5, wherein the bell crank device locks in the cocked position when the primary time delay device is in the engaged position and the bell crank device is operated for movement into the neutral position by the primary time delay device when the primary time delay device moves into the normal rest position.

7. The sanitizer apparatus as claimed in claim 4, wherein the bell crank device comprises a rotatable disc connected to the primary time delay device for rotation of the rotatable disc about a central axis of the rotatable disc through an arc, an actuating rod of the bell crank device connected by a first pivot pin to the rotatable disc for pivotal movement about an axis parallel to the central axis of the rotatable disc, said actuating rod of the bell crank device being connected by a second pivot pin to a spring-loaded pump actuating plate which engages the pump, rotation of the rotatable disc acting through the actuating rod of the bell crank device to move the spring-loaded pump actuating plate between a pump priming position and a pump discharge position.

8. The sanitizer apparatus as claimed in claim 7, wherein the first pivot pin is movable into an over-centre position in the cocked position to lock the bell crank device, the first pivot pin being movable out of the over-centre position in response to movement of the primary time delay mechanism out of the engaged position.

9. The sanitizer apparatus as claimed in claim 7, wherein a cocking pin is provided for connection to the door handle such that operation of the door handle causes translational movement of the cocking pin to move the primary time delay mechanism into the engaged position, wherein as the cocking pin moves the primary time delay mechanism into the engaged position, it also moves the bell crank device into the cocked position, the cocking pin having an elongate slot which engages a disc of the bell crank device actuating pin projecting outwardly from a face of the rotatable disc of the bell crank device, such that translational movement of the cocking pin causes rotational movement of the rotatable disc of the bell crank device.

10. The sanitizer apparatus as claimed in claim 9, wherein the primary time delay mechanism and the bell crank device are mounted on a support platform, the actuating rod or shaft and the cocking pin being movable parallel to the support platform, an elongate slot in the cocking pin engaging with a pin projecting outwardly from a face of the rotatable disc of the bell crank device to rotate the rotatable disc, the actuating rod of the bell crank device passing through an opening in the support platform and through a cylindrical housing to engage the spring-loaded pump actuating plate which has a tubular spigot slidably engaged with the bore of the cylindrical housing, a spring being mounted between the spring-loaded pump actuating plate and the cylindrical housing or the support platform to urge the spring-loaded pump actuating plate away from the support platform.

11. The sanitizer apparatus as claimed in claim 7, wherein a link arm is operably connected to the door handle, said link arm having an elongate slot for reception of a pin projecting outwardly from a front face of the rotatable disc of the bell crank device, translational movement of the link arm causing rotational movement of the rotatable disc of the bell crank device.

12. The sanitizer apparatus as claimed in claim 1, wherein a secondary time delay mechanism is provided to prevent actuation of the atomizing pump until the primary time delay mechanism is moved to the engaged position.

13. The sanitizer apparatus as claimed in claim 12, wherein the secondary time delay mechanism comprises a pendulum delay device.

14. The sanitizer apparatus as claimed in claim 13, wherein the pendulum delay device comprises a pair of pendulum plates which swing on pivots, lower edges of the pair of pendulum plates engaging and holding the atomizing pump in a discharge position until the primary time delay mechanism is in the engaged position, a plate on the actuating rod or shaft urging the pair of pendulum plates apart when the primary time delay mechanism is in the engaged position allowing the atomizing pump to move into a primed position.

15. The sanitizer apparatus as claimed in claim 1, wherein an actuator cam is operable to move the actuating rod or shaft of the primary time delay mechanism between the normal rest position and the engaged position and the actuator cam engages a roller rotatably mounted on a bracket connected to the actuating rod or shaft of the primary time delay mechanism for translational movement of the actuating rod or shaft.

16. The sanitizer apparatus as claimed in claim 1, wherein a bleed screw communicates between the narrow second portion of the bore of the associated fluid filled cylinder and an exterior of the associated fluid filled cylinder to control the rate of entry of air into the narrow second portion of the bore of the associated fluid filled cylinder.

17. The sanitizer apparatus as claimed in claim 1, wherein the piston is formed by a cup seal mounted on the actuating rod or shaft.

18. The sanitizer apparatus as claimed in claim 1, wherein the piston is axially movable on the actuating rod or shaft between spaced-apart stops, at least one port extending through the piston, a floating O-ring mounting in a circumferential channel in a side wall of the piston for movement between a disengaged position and an engaged position for sealing engagement between the piston and the narrow second portion of the cylinder bore portion of the associated fluid filled cylinder.

\* \* \* \* \*